(12) United States Patent
Heijman et al.

(10) Patent No.: US 10,136,763 B2
(45) Date of Patent: Nov. 27, 2018

(54) DOMESTIC APPLIANCES WITH POWER CONTROL

(71) Applicant: KONINKLIJKE PHILIPS N.V., Eindhoven (NL)

(72) Inventors: Edwin Heijman, Eindhoven (NL); Franciscus Jacobus Vossen, Eindhoven (NL); Roland Alexander Van De Molengraaf, Eindhoven (NL); Arno Zwenig, Eindhoven (NL); Thomas Strutzmann, Eindhoven (NL); Thomas Leonhard Sigot, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/319,035

(22) PCT Filed: May 21, 2015

(86) PCT No.: PCT/EP2015/061268
§ 371 (c)(1),
(2) Date: Dec. 15, 2016

(87) PCT Pub. No.: WO2015/197274
PCT Pub. Date: Dec. 30, 2015

(65) Prior Publication Data
US 2017/0143165 A1    May 25, 2017

(30) Foreign Application Priority Data

Jun. 27, 2014  (EP) .................................. 14174658.6

(51) Int. Cl.
*A47J 43/07* (2006.01)
*A61C 17/22* (2006.01)
*A47J 43/044* (2006.01)

(52) U.S. Cl.
CPC .......... *A47J 43/0716* (2013.01); *A61C 17/221* (2013.01); *A47J 2043/04427* (2013.01)

(58) Field of Classification Search
CPC ........ A47J 2043/04427; A47J 43/0716; A61C 17/221
See application file for complete search history.

(56) References Cited

U.S. PATENT DOCUMENTS

| 8,621,783 B2 | 1/2014 | Tsai | |
|---|---|---|---|
| 2004/0104826 A1* | 6/2004 | Philipp | G01D 5/24 341/34 |
| 2008/0197909 A1* | 8/2008 | Grosser | D06F 39/005 327/517 |

(Continued)

FOREIGN PATENT DOCUMENTS

| CN | 202698918 U | 1/2013 |
|---|---|---|
| CN | 202794927 U | 3/2013 |

(Continued)

*Primary Examiner* — Muhammad S Islam (57) ABSTRACT

A hand held domestic appliance comprises a handle part, a driven member, a motor for driving the driven member and a controller for controlling the motor. The handle part comprises a surface sensor for detecting a contact surface area and optionally also pressure and the controller is adapted to control the power supplied to the motor in dependence on the sensed contact surface area and optionally also pressure.

14 Claims, 5 Drawing Sheets

(56) References Cited

U.S. PATENT DOCUMENTS

| | | | | |
|---|---|---|---|---|
| 2013/0095925 | A1* | 4/2013 | Xu | G06F 1/1626 |
| | | | | 463/37 |
| 2013/0141387 | A1 | 6/2013 | Royhob | |
| 2014/0152610 | A1* | 6/2014 | Suwald | G01D 5/24 |
| | | | | 345/174 |

FOREIGN PATENT DOCUMENTS

| | | |
|---|---|---|
| DE | 29719596 U1 | 1/1998 |
| FR | 2823387 A1 | 10/2002 |
| JP | 03173558 A | 7/1991 |
| JP | 04236978 A | 8/1992 |
| JP | 07163421 A | 6/1995 |
| JP | 2011055934 A | 3/2011 |
| WO | 2005106335 A2 | 11/2005 |
| WO | 2012042493 A1 | 4/2012 |

* cited by examiner

DOMESTIC APPLIANCES WITH POWER CONTROL

This application is the U.S. National Phase application under 35 U.S.C. § 371 of International Application No. PCT/EP2015/061268, filed on May 21, 2015, which claims the benefit of International Application No. 14174658.6 filed on Jun. 27, 2014. These applications are hereby incorporated by reference herein.

FIELD OF THE INVENTION

This invention relates to hand held domestic appliances having a power adjustment function.

BACKGROUND OF THE INVENTION

Many domestic appliances have a power adjustment function, including kitchen appliances as well as personal grooming appliances.

For example, the electric motors in kitchen appliances (e.g. mixers, hand blenders, etc.) are typically controlled by knobs and rotary switches. These controls are not intuitive and since the controls will take over a large space, they will limit the freedom of design of the appliance.

There is therefore a need for a control input for power adjustment which is more intuitive for the user of hand held domestic appliances occupying less space.

DE 297 19 596 discloses a portable food processing device such as a hand blender in which a pressure pad is used to provide control of the motor speed.

Different users will have different hand strength and hand size, so that a pressure input device may not provide an interface which feels intuitive for all users.

SUMMARY OF THE INVENTION

The invention is defined by the claims.

According to the invention, there is provided a hand held domestic appliance comprising:
a handle part;
a driven member;
a motor for driving the driven member; and
a controller for controlling the motor,
wherein the handle part comprises a surface sensor for detecting a contact surface area and the controller is adapted to control the power supplied to the motor in dependence on the sensed contact surface area.

This appliance has an intuitive power control which relies on surface sensing rather than physical movement of a control button. Contact area sensing may for example be used to determine how many fingers are being applied to a surface sensor so that different numbers of fingers correspond to different desired settings. For example bringing a single finger into contact with the sensor part gives one speed setting and bringing another finger into contact gives another speed setting. In one example, this means a user is not required to apply any significant force to operate the device. By taking account of the sensed contact area, it is also possible to effectively block usage of certain dangerous appliances for infants and children.

The controller may be adapted to apply a user-defined calibration to the sensed contact surface area. This can be used to set thresholds below which the device will not operate and/or set thresholds for the different level settings.

The surface sensor may additionally be for detecting a pressure, and the controller is adapted to control the power supplied to the motor in dependence on the sensed pressure. In this case, the surface sensor is used to provide both area and pressure information. The way the power control varies as a function of pressure can then depend on the contact area. For example, for a small contact area, a lower pressure may be required for a given power setting, so that a smaller person does not need to press harder over that smaller area to achieve the same overall pressure level required for a particular power setting. In this way, a set of thresholds of both area and pressure can be applied which enable the most intuitive feel for the user. This feel can also be tailored to particular users of different hand size and strength.

The pressure control generally means that by pressing harder, the motor power (and therefore speed) can be increased, without needing to move the hand. This provides a more intuitive control methodology. It can also be used to provide safety solutions based on pressure levels (as well as or instead of based on area), again for example to block usage of certain dangerous appliances for infants and children.

The controller may be adapted to apply a user-defined calibration to the sensed pressure.

The user-defined calibration of area and/or pressure means that a threshold or set of thresholds can be personalized according to the calibration of the personal strain and/or size of the finger, fingers, palm or hand of the user. In this way, it becomes possible to tailor the function of the device to give a comfortable and intuitive feel for a particular user. The calibration comprises setting the relationship between the user applied pressure and/or contact surface area and the power supplied to the motor (which manifests itself as the motor speed).

The surface sensor typically has a larger area than a simple push button.

The surface sensor may have an outer surface which depresses by less than 1 mm for a range of applied pressures corresponding to the full range of power control. A layer of the surface sensor (which may or may not be the outer layer) may comprise a material which elastically deforms in response to the applied pressure. Alternatively, the layers may not deform but may move in response to the applied pressure, for example to vary an air gap or small gas pockets.

The speed control thus relies essentially on applied pressure rather than movement and the area over which this pressure is applied (even though the deformation of the sensor will give some movement).

The sensor may have an even smaller compression, for examples less than 0.5 mm or even less than 0.2 mm. Preferably a cover for example of a rubber, plastic sheet or foam with a thickness for example in the range of a few micrometers to a few millimeters can be used to cover or surround the sensor.

The surface sensor may comprise two electrode arrays embedded in a deformable dielectric material or between which a dielectric material layer is sandwiched. Pairs of electrodes define individual pressure/contact sensors, and by providing an array the sensor can also detect the localities at which pressure is applied.

This provides a simple sensor structure which can detect local capacitance changes. Electrical contacts are simply needed to the electrodes of the two electrode arrays for measurement using a detection circuit which can be implemented with low cost. Each individual pressure sensor may use more than two electrodes in a stacked configuration to give increased capacitance.

An alternative is a layer filled with conductive particles. When a pressure is applied the distance between particles can be reduced, giving a change in conductance/resistance.

The surface sensor may have an area in the range 2 $cm^2$ to 30 $cm^2$.

The sensor area will depend on the type of control being implemented. For detecting a finger pressure an area of 2 $cm^2$ to 5 $cm^2$ may be used for each finger forming part of the control. For detecting a palm pressure/area or overall grip tightness, a larger area of 5 $cm^2$ to 30 $cm^2$ may be used.

To implement a large area sensor, an area in the range 10 $cm^2$ to 30 $cm^2$ may be used. A large sensor area also enables the sensor to be responsive to the overall contact area and optionally also the pressure applied.

The surface sensor may comprise contacts at the back of the sensor. This enables simple application to a surface of the appliance for example by gluing.

The sensor can be designed for operation by a single finger, fingers, palm or by the overall grip of the hand. These different possibilities will give rise to different preferred sizes within the general range. A large area for detecting the whole hand can give rise to safety benefits, for example preventing operation by small children.

The controller may comprise:

a resistor in series with a capacitor defined by the surface sensor;

a discharge switch for discharging the capacitor; and a timing circuit for timing the charging of the capacitor from a discharged state to a reference voltage and for controlling the switch to implement capacitor discharge.

This provides a simple circuit for measuring capacitance, by measuring the charging time through a known resistor. The actual capacitance does not need to be derived, in that the timing measurement provides a control signal which depends on the capacitance.

The timing circuit preferably performs a discharge and timing operation periodically. The circuit can thus periodically monitor the applied pressure when turned on. The period is for example in the range 1 ms to 100 ms. The period is low enough that the speed can be adjusted during operation, and high enough for the required signal processing to be kept simple.

The timing circuit may comprise a counter which runs at a faster frequency than the frequency of the discharge and timing operations.

The same counter can in this way control the timing of the periodic discharge as well as the measurement of the time duration for charging the capacitor. The controller may be a low cost standard micro-controller.

The controller may be adapted to apply one of a set of motor speeds in dependence on the surface sensor output. The set of motor speeds may be selected based on the type of appliance and the number of different speed settings suitable for that appliance. The set of motor speeds may comprise a zero speed, a full speed and at least one intermediate speed.

The appliance is preferably held continuously during use and the power is adjustable during use. The ease of use of the surface sensor is of particular interest for such devices.

In one set of examples, appliance may comprise a kitchen appliance, wherein the driven member comprises a food processing member, and the appliance comprises one of:

a bar blender;
a mixer;
a chopper;
a food processor;
a grinder;
a juicer.

In another set of examples, the appliance may comprise one of:

an oral healthcare device such as a toothbrush;
a grooming appliance such as a shaver.

The invention can thus be applied to a large range of domestic appliances, to give increased user comfort and intuitive control.

The invention also provides a method of controlling a hand held domestic appliance comprising a handle part, a driven member and a motor for driving the driven member, wherein the appliance comprises a surface sensor provided at the handle part of the appliance for sensing a contact surface area, wherein the method comprises:

detecting a contact surface area using the surface sensor; and controlling the power supplied to the motor in dependence on the sensed contact surface area.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a hand held domestic appliance comprising a handle part, a driven member, a motor for driving the driven member and a controller for controlling the motor. The handle part comprises a surface sensor for detecting a contact surface area and/or pressure and the controller is adapted to control the power of the motor in dependence on the sensed contact surface area and/or pressure. The operation of the surface sensor may be calibrated to a particular user.

This provides an improved control mechanism for motors in domestic appliances (such as mixers or hand blenders) because the sensor may for example be incorporated into the grip of the appliance, or at the natural touch position for the hand and/or finger. Often different levels of control (e.g. motor speed) are required, so the sensor can measure the applied pressure/force or area to provide the different control levels. Furthermore, the thresholds for these pressure or area signals may be set as part of a user calibration operation.

As the sensor is for surface mounting, it may be deformable, water resistant and easy to clean.

Figure 1:
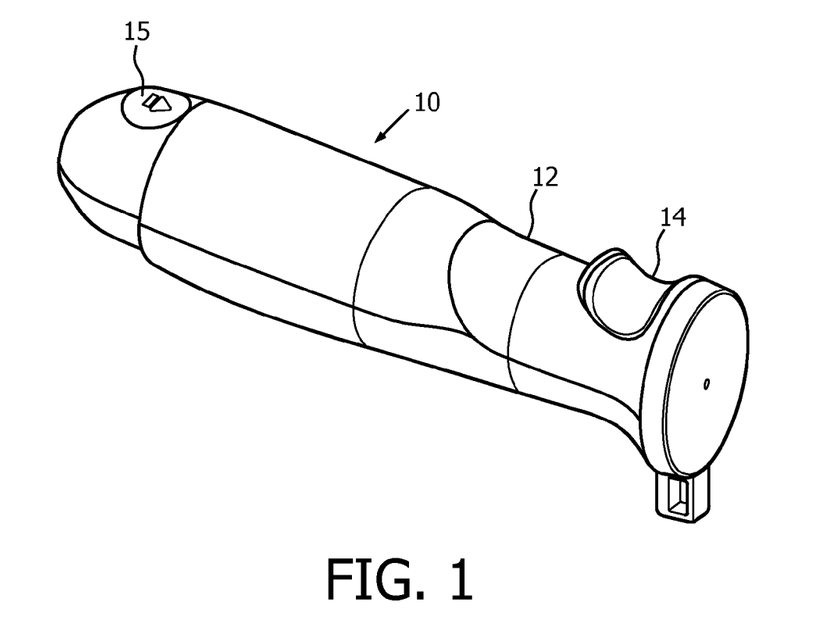
FIG. 1 shows an example of appliance in the form of a bar blender.

FIG. 1 shows a first example of bar blender using the sensor arrangement of the invention, in perspective view.

The blender comprises a main housing 10 having a handle grip portion 12. A surface sensor 14 is at the handle grip portion for controlling the motor speed. In this example, the surface sensor is positioned at the location of the user's fingers when gripping the handle. A release button 15 enables fitted attachments such as a blending tool or whisking tool to be swapped over.

The sensor is a surface sensor, by which is meant that it detects surface pressure and/or area. The movement of the sensor when operated by the user is less than a push button or push slider. For example the sensor preferably has an outer surface which depresses by less than 1 mm for a range of applied pressures corresponding to the full range of power control. The deformation may be significantly less, for example less than 0.5 mm or less than 0.2 mm.

The surface sensor is used to detect a contact surface area, and optionally also an applied pressure.

The surface sensor provides a more intuitive control compared to a switch or rotary knob. For blending potatoes or pumpkin soup where a firmer grip is necessary, the use of pressure sensing means the firmer grip automatically results in increased power to the motor when the blender is pressed into the vegetables.

The sensor preferably uses deformable materials rather than components which move mechanically. In this way, moving mechanical parts are replaced with static surface sensor components. This gives a more intuitive interface compared to a mechanical control structure. A greater freedom of the design is also enabled. By making the sensor from compliant materials, the outer shape and material can be freely selected. For example this makes it easy to provide waterproofing, easily cleanable designs, and antibacterial properties.

By eliminating moving mechanical parts, space saving benefits are also obtained. Only the sensor thickness needs to be considered. The thickness including a cover can be in the range of a few micrometers to a few millimeters. The assembly process is also simplified, for example the sensor 14 can be applied by gluing.

Figure 2:
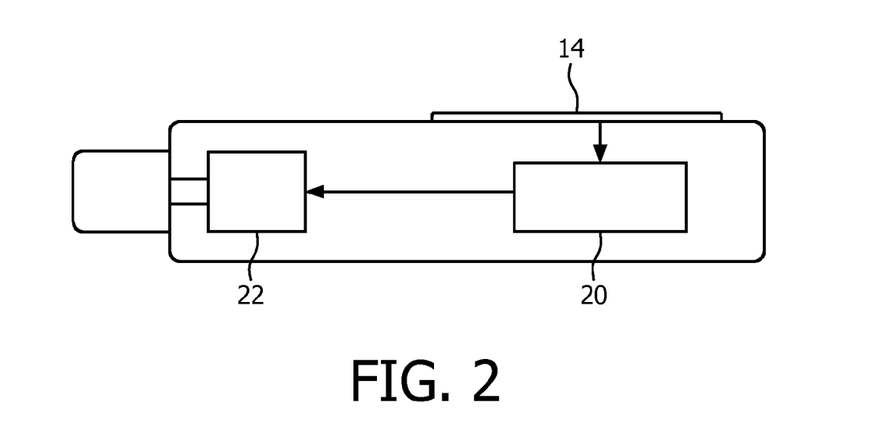
FIG. 2 shows the control system used in the appliance of FIG. 1.

FIG. 2 shows the overall system. The surface sensor 14 provides its output to a controller 20 which drives the motor 22 of the appliance.

Figure 3:
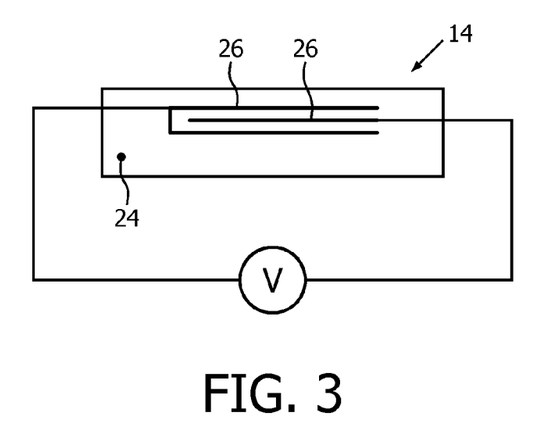
FIG. 3 shows one example of surface sensor for use in the appliance of FIG. 1.

FIG. 3 shows a first example of the sensor 14. This example is a capacitive pressure sensor, which comprises a deformable dielectric material 24 which is sandwiched between (and optionally also surrounding) compliant electrodes 26. Single sensor elements can be stacked on top of each other to increase the initial capacitance.

By encapsulating the electrodes in the dielectric material 24 as shown, capacitive interference is reduced. The electrode facing the user's hand is also selected to be the common ground electrode.

The sensor is designed to be suitable to be applied to kitchen appliances or other domestic appliances. This requires the sensor to be compliant and sensitive in the range of the induced pressure of a human hand. The minimum required capacitance should be high enough to avoid interference from the surroundings, for example greater than 1 pF for a capacitive sensor as shown. The capacitance change corresponding to a full pressure range should be detectable in a reliable way.

The capacitive sensor can have a large area, for example greater than 1 cm$^2$ and optionally up to around 30 cm$^2$. The sensor is for example located at the grip of the appliance as shown in FIG. 1 for a device to be used with one hand. However, it may be provided at a separate touchable surface of the handle part, for example if the device is designed to be used with two hands.

The sensor may have for example solid thin metal electrodes or carbon electrodes with a soft compliant polymer between to ensure the deformability of the configuration. Alternatively, an electroactive polymer can be sandwiched between compliant electrodes offering a high electromechanical efficiency. Another possible design is a layer filled with conducting particles at a certain distance from each other. By applying pressure, particles will move closer to each other, giving a change in conductance/resistance.

The structure of the deformable capacitive sensor shown in FIG. 3 is comparable to other tactile feedback actuators. The sensor is formed in layers to embed the electrodes inside a dielectric material.

The deformable dielectric material can be chosen according to its Young's Modulus (defining the compressibility) and the dielectric constant (determining the capacitance properties). The dielectric can be an elastomer, such as silicone, acrylic or polyurethanes. Other electrostrictive materials may be used, such as Poly(vinylidene fluoride) (PVDF) and PVDF based copolymers and terpolymers because of their high dielectric constant. Industrial polymers such as polyethylene, polyimide and polypropylene as well as several types of rubber may be used, which can give a lower cost. The dielectric material properties can thus be selected for different ranges of pressure/force, dielectric value and encapsulating layers by changing the material.

The electrodes can be made out of metal, carbon or other compliant conducting materials. Several electrode materials can be used. As long as the strain stays below +/−5%, most metal electrodes can be used. If larger strains are needed in the final design, conductive polymers such as PEDOT, PEDOT-PSS and PANI may be preferred. For very large strains, carbon particles or carbon grease can be a suitable option.

The controller 20 has a number of different functions, including detection of the capacitance change, threshold functions to prevent control changes based on non-user events, calibration and safety measures or user functions (like cruise control, etc) or feedback.

A calibration function can involve the user being prompted to apply a light pressure, a medium pressure and a high pressure. The controller can then derive suitable threshold values (the values 16, 17, 28, 29, 31 used in steps 64,66,68 in FIG. 6 described below) in order to adapt the operation of the device to the particular characteristics of the user.

Various approaches are possible for measuring a variation in capacitance.

Figure 4:
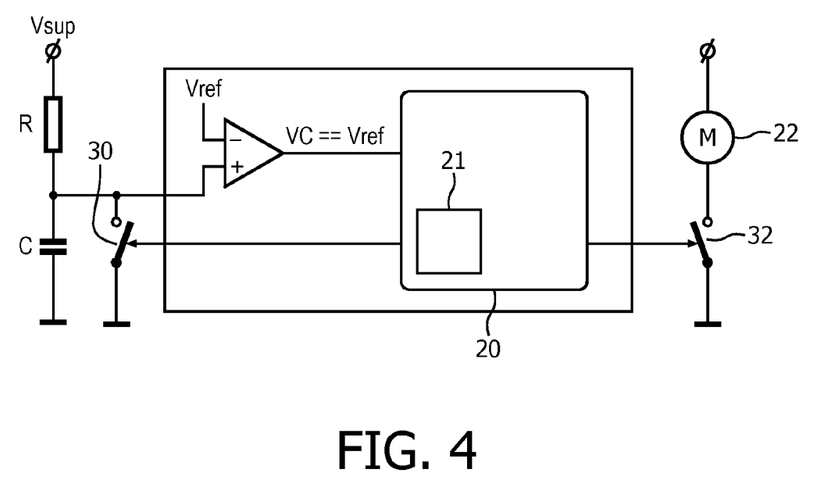
FIG. 4 is used to show how the sensor capacitance can be measured.

One simply approach is to inject a well-defined current to the capacitance through a series resistor. The voltage build up is defined by the equations below. Since all, but one, parameters in these equations are constants, the time to charge the capacitance to a reference voltage (Vref) is linearly related to the capacitance value (C).

$$VC(t) = \frac{1}{C}\int_0^t i(t)\,dt = Vsup \cdot [1 - e^{\frac{-t}{RC}}]$$

$$VC(t) = Vref : t = RC \cdot \ln\left[\frac{Vsup}{Vsup - Vref}\right]$$

Vsup is the supply voltage, Vref is the reference voltage to which the capacitor is charged and C is the capacitance. VC(t) is the capacitor voltage as a function of time, and R is the series resistance.

FIG. 4 shows the capacitance C, resistor R, and supply voltage Vsup.

The controller 20 includes a counter 21 (implemented in software based on the clock of the controller) for timing control. The controller controls a discharge switch 30 which is in parallel with the capacitance, and controls a switch 32 for driving the motor 22.

The controller may for example discharge the capacitance every 10 ms. Subsequently charging of the capacitance via the series resistor is initiated, and the controller monitors the elapsed time. When the capacitor voltage VC(t) reaches the reference voltage Vref, the elapsed time is read out and used for calculating a duty cycle for driving the motor.

Figure 5:
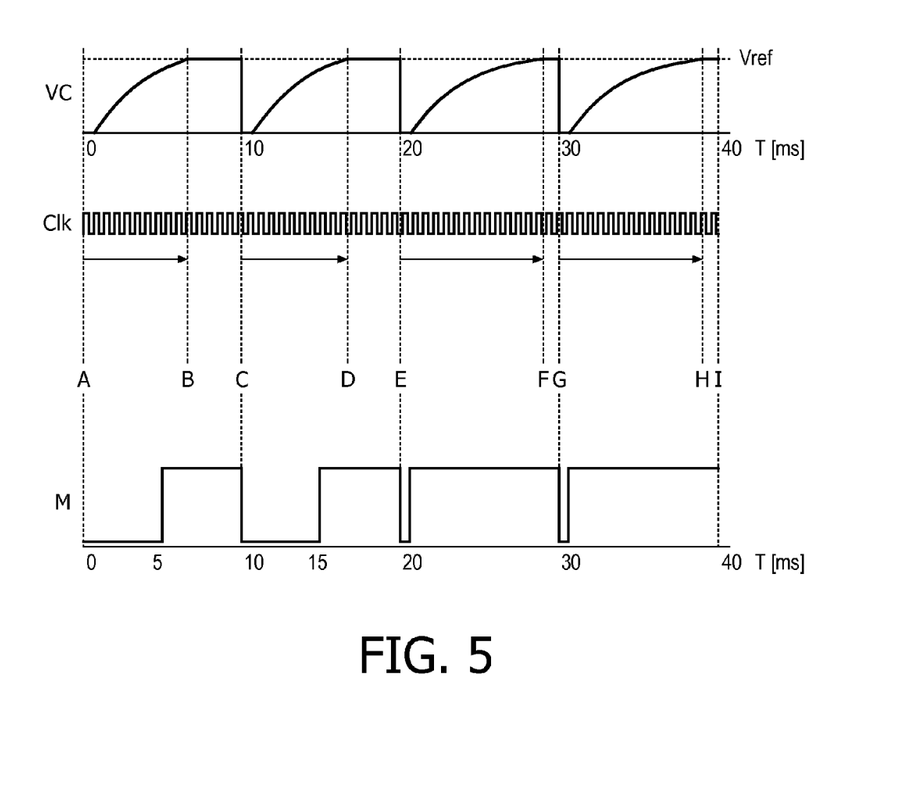
FIG. 5 is a timing diagram to explain the operation of the appliance of FIG. 1.

FIG. 5 is a timing diagram to explain the operation of the sensor. The top plot (VC) shows charging curves for the capacitor. The bottom plot (M) shows the motor drive signal, and the middle plot (Clk) shows the controller clock signal which is used as a timing counter. The timing counter has a frequency of 3.2 kHz so that there are 32 clock cycles in each 10 ms period.

If little pressure is applied, the capacitance value will be relatively low, and therefore the time it takes for charging up to the reference voltage Vref is relatively short. This is indicated by the first two charging curves in FIG. 5, between time point A and B and between time points C and D.

At time points A and C, the capacitor is discharged ready for the charging cycle. At time points B and D a clock counter of the controller is read out as a measure of the elapsed time.

The relatively low pressure gives rise to duty cycle of 50% as shown in the bottom plot.

More pressure is applied at time point E, so that the capacitance value increases and with it the time it takes to charge to Vref. The capacitor discharge and timing count functions in the same way. The duty cycle then becomes is close to 100% (high pressure). To have a smooth running motor under all conditions the frequency is for example fixed at 100 Hz giving the 10 ms period of the motor control signal.

The controller operates various processes.

The first is a count from 0 to 31 running at the 3.2 kHz clock rate. This can be implemented as a 5 bit counter. The counter is initialized to keep on counting cycles of the clock. At the start of charging, the counter is reset and started to monitor the time it takes for VC to reach Vref. Based on the counter value when Vref is reached, a desired duty cycle is calculated and used for driving the motor.

Figure 6:
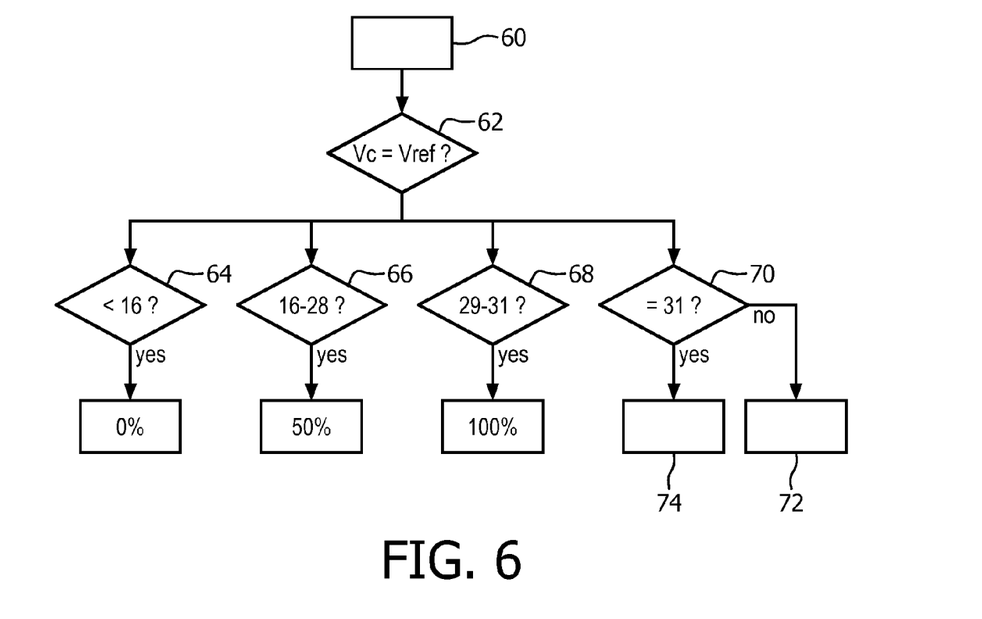
FIG. 6 is a first flow chart to explain the operation of the controller used in the appliance of FIG. 1.

A second is an analysis of the clock counter value when the voltage reaches the sense voltage. This process is shown in FIG. 6.

At the time when VC reaches Vref, the clock counter value is compared with a set of thresholds.

The process starts in step 60, and then waits in step 62 for VC to reach Vref.

The counter value is then compared with thresholds.

The comparison of step 64 sets the motor off if the clock counter is below 16, indicating a very low applied pressure.

The comparison of step 66 sets the motor to a 50% duty cycle off if the clock counter is between 16 and 28, indicating a medium applied pressure.

The comparison of step 68 sets the motor to a 100% duty cycle off if the clock counter is between 29 and 31, indicating a maximum applied pressure.

Thus, the duty cycle for the motor (DC) takes the following values in dependence on the count value:

Count<16→DC=0%,

Count=22±6→DC=50%,

Count=30±1→DC=100%

In step 70 it is determined if the cycle is finished, when the count reaches 31. If it is finished, there is a discharge step 72, otherwise charging continues in step 74.

In FIG. 6 only three different duty cycles are given, 0%, 50% and 100%. However, this can easily be increased to any other number. If more levels are needed the clock frequency may be increased.

As mentioned above, the values used in the threshold testing steps 64,66,68 can be adjusted by the user, either based on an initialization sequence, or as parameters which the user can input to the controller through a user interface.

In this way, the device implements a user-defined calibration to the contact surface area and/or pressure.

One way to implement this calibration is for the device to have a user calibration mode. During this mode, the device may request a very light applied pressure or small contact area to be applied to the handle, then measure the capacitance in the same way as described above. For a sensor array (as described below) it may also determine the area independently of the pressure applied. The device may then request a maximum applied pressure or contact area, and again measure the capacitance in the same way as described above, and again it may independently determine the contact area. From these two extreme values, two thresholds may be set, or else three or more thresholds can be extrapolated. Thus, the user calibration mode may instead request more than two user input pressures or contact areas to be applied.

In the discussion below, when reference is made to pressures, the same concepts apply to the use of contact area as the control parameter.

A single input may be sufficient during the user calibration, which defines the the maximum pressure the user would like to apply, and threshold values can then be set between a fixed minimum pressure and the maximum pressure as input by the user. Instead of being fixed, the minimum pressure level may be assumed to be a fraction of the maximum pressure as input by the user (e.g. one half of that pressure).

The device may provide operation of the food processing member during this user calibration mode, so that the user has a good feel for the way the device is behaving when deciding what pressure level should correspond to this behavior. Alternatively, the user calibration may be performed without the motor running.

Multiple user profiles may be entered so that a device which is shared between multiple people can be configured separately for those different users. The user can then for example input which user they are for example using a set of input buttons, each one corresponding to a different device configuration.

Figure 7:
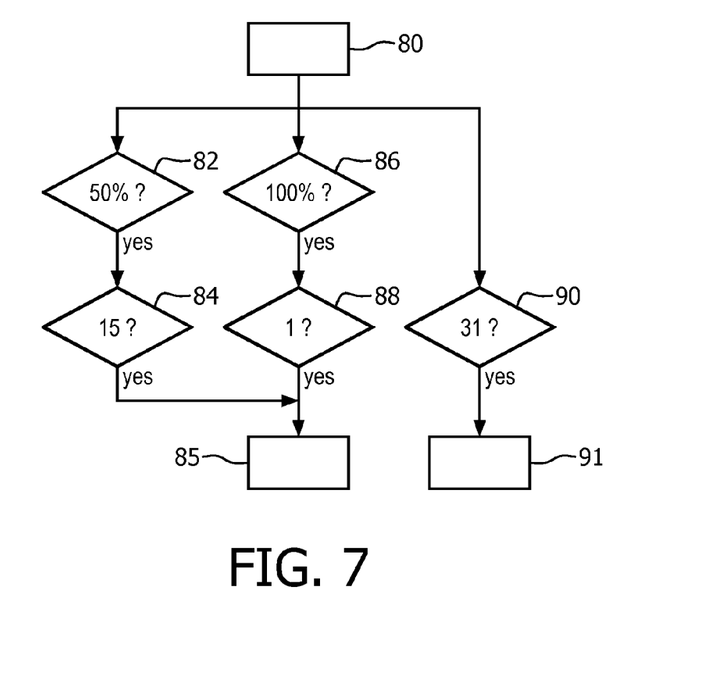
FIG. 7 is a second flow chart to explain the operation of the controller used in the appliance of FIG. 1.

FIG. 7 shows the process for controlling the motor. The process starts in step 80. Step 82 determines if the duty cycle setting is the 50% value. If so, when the counter reaches 15 as determined in step 84 the motor is started in step 85.

Step 86 determines if the duty cycle setting is the 100% value. If so, when the counter reaches 1 as determined in step 88 the motor is started in step 85.

The motor continues until stopped by a subsequent stop command. In particular, step 90 determines when the counter reaches 31 and the motor is then stopped in step 91. Thus, even the 100% duty cycle setting has a zero pulse of duration one clock cycle to give a 100 Hz signal.

The sensor can be designed to provide additional safety benefits, particularly if a large area sensor is used.

A large area sensor may have an area of 10 cm² to 30 cm².

As mentioned above, the surface sensor is able to measure a contact area and optionally also a pressure. There are various possible designs for the surface sensor, so that it can either measure only the area, or else it can measure independently the area and the pressure.

A first design may detect contact area only. For this purpose, an array of pressure sensors may be provided over the area of interest. Each pressure sensor can generate a simple binary output, so that each individual pressure sensor functions as a contact sensor. Other contact-only sensors may be used for this purpose, and these may also be capacitive sensors. The number of sensors where contact is detected can be used to determine a contact area. Different areas (and the location of those areas) can then relate to different speed settings. For example, there may be sensing areas at finger pads and at a palm area, so that the number of fingers contacting the sensor is detected. A threshold level can then be used to ignore a palm and/or fingers below a threshold size, to prevent operation by children. The number of finger areas which are contacted can then provide speed control, whereas the overall area or the palm area can provide a threshold to prevent operation by small children.

A second design may detect contact area and pressure. For this purpose, an array of pressure sensors may be provided over the area of interest. Each pressure sensor can generate a multi-level pressure output, so that each individual pressure sensor functions both as a contact sensor (i.e. if any pressure is detected at all) and also as a pressure sensor. Again, the number of pressure sensors where any contact at all is detected can be used to determine a contact area. The pressure level information can also be used to determine local pressure levels and an overall pressure applied. Different pressure levels can then relate to different speed settings, while additionally incorporating thresholds which may be based on area and optionally also pressure. For example, there may be sensing of a hand palm size to provide an effective safety feature, in addition to control which is then based essentially on pressure. In this way, the device can combine effective safety features as well as intuitive control. In this example, the surface sensor is able to detect contact area and pressure independently.

Note that a capacitive sensor may be used as a contact area sensor even if it comprises a single sensor area. In particular, if there is essentially a binary change in local dielectric permittivity in response to the applied contact or pressure, and thus a binary change in local capacitance, then a small contact area will result in a smaller capacitance change compared to a large area contact area (regardless of the pressures applied).

The use of area as a safety threshold also enables implementation of a safety feature in that erroneous activation if the device is dropped is less likely, as well as making activation by children more difficult.

If the sensor responds not only to the contact area, but also the pressure applied, then a threshold may be set which is achieved by a combination of the applied area and force.

Other sensors may be used to detect the contact area and optionally also the pressure. The controller can also filter out short peaks which cannot be generated by a human being.

By designing the shape and setting the thresholds appropriately, the sensor can be made particularly suitable for the elderly or disabled.

Figure 8:
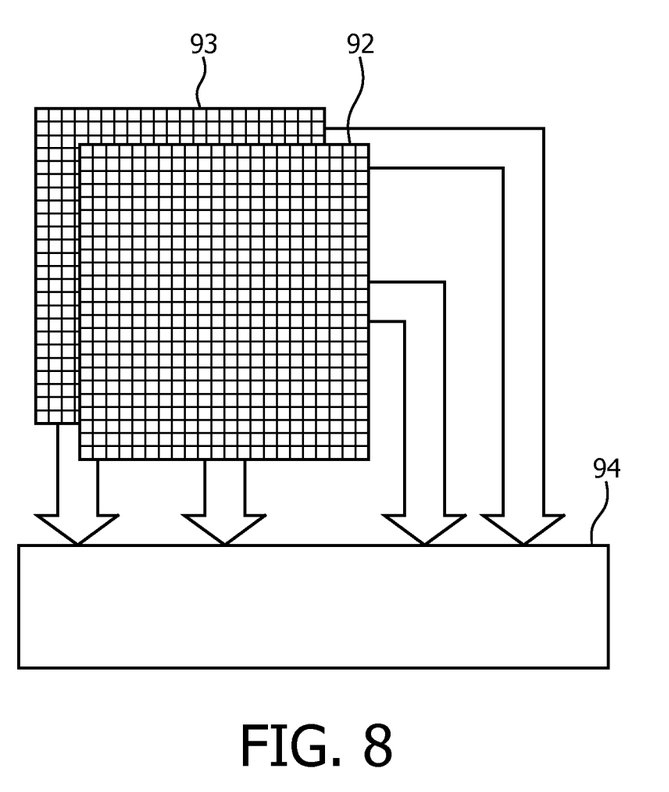
FIG. 8 shows a surface sensor arranged as an array of surface sensor elements.

FIG. 8 shows in schematic form how a sensor array may be used, which comprises an array of independent sensor elements. The sensor array in this example comprises first and second electrode arrays 92,93 which define an array of independent capacitive pressure sensors. The electrode signals are routed to the controller 94. As described above, the pressure sensors may function only as contact sensors so that the number of activated sensors relates to a contact area, or else each sensor may also provide a pressure indication, so that the surface sensor then enables more involved processing of both area and pressure information.

The sensor can be used to implement additional functions. For example, a sequence of pressure applications, or applications of contact to a sequence of sensing areas, can be recognized, for example to provide a cruise function if the sensor is pressed twice.

The sensor can be combined with a system which incorporates tactile feedback.

The sensor can be glued on the appliance during production, with only a feed-through needed for the electric connectivity to the driver electronics. For this purpose, the contacts to the sensor can be provided on the face of the sensor opposite the area where user input is provided.

The example above is based on a sensor which detects a change in capacitance, but another impedance values may be modulated and read out by the surface sensor. The motor is controlled by pulse width modulation in the example above, but other motor controls may be used, for example varying the supply voltage as a function of the sensed value.

The system makes use of a controller. Components that may be employed for the controller include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A hand held domestic appliance comprising:
   a handle part comprising:
      a surface sensor configured to provide both area and pressure information, said surface sensor configure to:
         detect
            a size of a contact area with said surface sensor; and
            a pressure associated with said contact;
   a driven member;
   a motor for driving the driven member; and
   a controller configured to:
      receive from said surface sensor:
         said size of said contact area, and
         said pressure associated with said contact; and control a power supplied to the motor,
wherein the power applied to the motor varies based on the said size of said contact area and said pressure.

2. The hand held domestic appliance as claimed in claim 1, the controller configured to:
apply a user-defined calibration to the contact area.

3. The hand held domestic appliance as claimed in claim 1, the controller configured to:
apply a user-defined calibration to the pressure.

4. The hand held domestic appliance as claimed in claim 1, wherein the surface sensor comprises:
an outer surface configured to:
depress by less than 1 mm, wherein said depression corresponds to a pressure associated with a contact.

5. The hand held domestic appliance as claimed in claim 1, wherein the surface sensor comprises:
at least two electrode arrays with a deformable dielectric material in between.

6. The hand held domestic appliance as claimed in claim 1, wherein the surface sensor has an area in a range of 2 cm$^2$ to 30 cm$^2$.

7. The hand held domestic appliance as claimed in claim 1, wherein the surface sensor comprises electrical contacts.

8. The hand held domestic appliance as claimed claim 1, wherein
the surface sensor comprises:
a capacitive pressure sensor, and
the controller comprises:
a resistor (R) in series with a capacitor (C) defined by the capacitive pressure sensor;
a discharge switch configured to discharge the capacitor; and
a timing circuit configured to time the charging of the capacitor from a discharged state to a reference voltage; said controller configured to:
control the discharge switch to implement capacitor discharge.

9. The appliance as claimed in claim 1, wherein the controller is configured to:
apply one of a set of motor speeds in dependence on a surface sensor output.

10. The appliance as claimed in claim 1, wherein the power is variably adjustable during use.

11. The hand held domestic appliance as claimed in claim 8, wherein the timing circuit is configured to:
perform a discharge and timing operation periodically, wherein the timing circuit comprises:
a counter configured to run at a frequency faster than a frequency of the discharge and timing operation.

12. The appliance as claimed in claim 10 wherein the appliance comprises:
comprises one of:
a kitchen appliance;
a bar blender;
a mixer;
a chopper;
a food processor;
a grinder;
a juicer;
an oral healthcare device,
a toothbrush;
a grooming appliance and
a shaver.

13. A method of controlling a hand held domestic appliance comprising a handle part, a driven member and a motor for driving the driven member, wherein the hand held domestic appliance comprises a surface sensor provided at the handle part of the appliance for sensing a contact surface area and a pressure on said contact surface area, wherein the method comprises:
detecting a contact with said contact surface area;
determining a size of an area associated with said contact and a pressure applied to the contact surface area; and
controlling a power supplied to the motor in dependence on the size of said area and the pressure,
wherein the power supplied to the motor varies based on the pressure and the size of said contact area.

14. The method as claimed in claim 13, further comprising:
setting a threshold counter value based on at least the contact surface area and the pressure applied to the contact area, wherein the threshold counter value represents a value for determining conditions for supplying the power to the motor.

* * * * *